United States Patent [19]
Shen et al.

[11] Patent Number: 6,002,003
[45] Date of Patent: Dec. 14, 1999

[54] CYANINE DYE ACTIVATING GROUP WITH IMPROVED COUPLING SELECTIVITY

[75] Inventors: Gene G.-Y. Shen, Diamond Bar; Thomas S. Dobashi, Rosemead, both of Calif.

[73] Assignee: Beckman Instruments, Inc., Fullerton, Calif.

[21] Appl. No.: 09/059,900

[22] Filed: Apr. 14, 1998

[51] Int. Cl.$^6$ .............................. C07F 9/09; C07F 9/141; C07D 207/408; C07D 487/04

[52] U.S. Cl. .......................... 544/232; 544/277; 544/317; 546/23; 546/24; 548/113; 548/547; 548/548; 548/549; 548/579; 548/565; 548/453; 549/473

[58] Field of Search .................................... 544/232, 277, 544/317; 546/23, 24; 548/113, 547, 548, 549, 579, 565, 453; 549/473

[56] References Cited
PUBLICATIONS

Evangelista et al, Characterization of Fluorescent Nucleotide Triphosphates . . . , Analytical Biochemistry, 235, 89–97, Dec. 1996.

*Primary Examiner*—Johann Richter
*Assistant Examiner*—Dominic Keating
*Attorney, Agent, or Firm*—William H. May; P. R. Harder; Irell & Manella

[57] ABSTRACT

Activating groups for cyanine dyes used to label chain terminators in nucleotide sequencing, based on N-hydroxyphthalimide, are disclosed. From these activating groups, activated dyes of the present Invention are prepared which react with the derivitized nucleotide chain terminators to give a labeled chain terminator of the present Invention. The activating groups of the present Invention allow the dye-chain terminator reaction to occur at a much higher yield and with much greater selectivity for the monosubstituted product, compared with the prior art.

25 Claims, 10 Drawing Sheets

Cy7

Cy5

DBCy5

DBCy7

Cy7

DBCy5

Cy5

DBCy7

CYANINE DYE ACTIVATING GROUP WITH IMPROVED COUPLING SELECTIVITY

BACKGROUND OF THE INVENTION

1. Technical Field of the Invention

This invention relates to the preparation and use of activating groups for enhancing the reactivity between fluorescent dyes and nucleic acid chain terminators, for use in nucleic acid sequencing methods.

2. Prior Art

The present Invention relates to novel families of compound for use in nucleic acid sequencing. More specifically, the present Invention discloses and claims compounds (as well as their method of synthesis) for use as activating groups. More specifically, these compounds act as linking agents to allow the attachment of fluorescent dyes to certain derivatized nucleotides, and thus enabling the investigator to determine the sequence of the bases on the nucleic acid chain of interest. What follows is a brief description of a typical experimental setting for the novel compounds of the present Invention to provide context and to assess the advantages of the present Invention over the prior art. Finally, the compounds used in the prior art shall be discussed.

The most fundamental information regarding a particular nucleic acid isolate is its sequence—that is, the nucleotide bases that make up the isolate and the precise order of these bases on the molecule. For example, DNA is a large molecule, often presented visually in the shape of a ladder. This ladder is actually comprised of two mirror image pieces, each piece comprising a single vertical brace to which the rungs are attached, and one half of each rung. Thus the "half rungs" of each piece or strand fit together to form a complete ladder. The rungs of the ladder correspond to nitrogenous bases; in the case of DNA, there are only four types: adenine (A), guanine (G), cytosine (C), and thymine (T). Each rung therefore consists of two bases. Moreover, the two bases comprising each rung can only be certain complementary pairs: A can only fit with T, and G can only fit with C; thus, a rung can be A-T, G-C, T-A, or C-G, but not T-G, for instance. Significantly, this means that if the sequence of one piece of the ladder is known, then the other sequence can be readily determined since it can be inferred from the requiring pairings. This latter strand is known as the "complementary strand." In summary, "sequencing" a DNA strand means determining the identity and order of its rungs (or actually half rungs), e.g., A-T-G-C-A, etc. Knowledge of this sequence allows investigators to determine the proteins encoded by that sequence and to compare that sequence with others of known function.

At present, several nucleic acid sequencing methods are widely used. One is the dideoxy chain termination method, discussed in Sanger et al., Proc. Natl. Acad. Sci. 74:5463–67 (1977). This reference is hereby incorporated by reference into the present Application. Another is the chemical degradation method, discussed in Maxam et al., Proc. Natl. Acad. Sci. 74:560–564 (1977); a third group is the hybridization methods, discussed in Drmanac et al., Genomics 4:114–28, and Khrapko, FEB 256:118–22 (1989). Of these, the dideoxy chain termination method disclosed in Sanger et al. is the one to which the present Invention is primarily, though not exclusively directed.

Briefly, the Sanger et al. method involves isolating a single strand of the nucleic acid of interest, which will be used as a template for primed synthesis of a complementary strand. It is this complementary strand whose sequence will be determined; the sequence of the original strand can then be inferred. To determine a sequence of a DNA strand using the Sanger et al. method, the complementary strand is constructed using the original strand as a template. To construct a complementary strand, four different reaction vessels are used—which correspond to the four types of bases comprising DNA—A, T, G, and C. To the first reaction vessel, the original strand is added (which acts as the template upon which synthesis of the complementary strand occurs) along with DNA polymerase, which catalyzes the synthesis of the complementary strand; and finally, the bases (A, T, G, and C) are added which are the building blocks for the new strand. Some of one group of bases (either of the four) per reaction vessel is derivatized; that is, it is chemically altered such that no further synthesis of the strand can occur after that base is added to the chain of bases comprising the complementary strand. Thus, in the first reaction vessel, some of the "A" bases will be derivatized so that chain synthesis stops (i.e., no further synthesis can occur) upon incorporation of that derivatized base into the DNA strand. This derivatized base is called a "chain terminator." In the reaction vessel, millions of DNA complementary strands are being synthesized, since both normal "A" and the derivatized version of "A" (i.e., the chain terminator) are added to the reaction vessel; some strands will incorporate normal "A," others the chain terminator, still others will incorporate the chain terminator at the second occurrence of A on the chain (i.e., where the original strand as a "T"), still others the third, and so forth. Thus, after some time, the reaction vessel will contain a mixture of partial complementary strands of various chain lengths, depending upon at what point in the sequential synthesis they were terminated. They all have one common feature: they all stop at an "A" caused by incorporation of the chain terminator into the complementary strand. Therefore, the investigator can in theory determine every point on a hypothetical complete complementary strand at which an "A" occurs. This is true because if there are millions of partially synthesized complementary strands in the vessel, one would expect— statistically—that there would be found in that vessel at least one partially synthesized chain (that must terminate at "A") corresponding to every occurrence of an "A" in the hypothetical completed complementary strand. Thus, if the hypothetical completed complementary strand had 100 "A" bases in it, then one would expect 100 partially synthesized complementary strands of different lengths, since the synthesis of each one would have stopped upon incorporation of a chain-terminating "A" (though not by incorporating a normal "A"). Obviously, if the same method is performed in three other reaction vessels for T, G, and C, then the entire sequence of the complementary strand can be determined.

What is needed therefore is some means to "mark" or "tag" the chain terminators so that they can be identified. This allows the investigator to determine precisely when the chain stopped; this information is valuable because the investigator now knows what base is present at the point of termination (in our prior example, it would be "A"). One means that has proven quite successful is to attach cyanine dyes to the chain terminators. These dyes fluoresce when exposed to ultraviolet light, thus signaling their presence. For reasons which shall be discussed below, affixing the dyes to the chain terminators is problematic. Thus, the present Invention is directed to a family of compounds that enables the dye and chain terminator to be readily affixed.

The process of affixing the dye to the chain terminator typically involves derivatizing the dye, or "activating" the dye. Compounds, such as those disclosed in the present Invention which activate the dye, are typically referred to as "activating groups." Presently, para-nitrophenol (PNP) and N-hydroxysuccinimide (NHS or Osu) are used as activating groups for cyanine dyes. Thus, these compounds allow the coupling reaction between dideoxynucleotides-amine (ddNTP-NH2) and the cyanine dye, which results in the desired dye-labeled terminator. These activating groups of the prior art (PNP and NHS) have numerous shortcomings though. First, the coupling of dye-PNP with ddNTP gives a lower yield than that of dye-NHS. Second, and most significantly, both dye-PNP and dye-NHS give a mixture of two major products, namely the mono-substituted product and di-substituted product (i.e., two chain terminators per dye molecule). This is undesirable. Consequently, a large excess of activated dye is needed for the coupling reaction in order to favor the formation of the mono-substituted product. Finally, the prior art activating groups give relatively low yields of the desired product.

The present Invention is directed to a novel family of activating groups designed to provide greater selectivity for the mono-substituted product over the di-substituted. The activating groups of the present Invention also provide greater yields of the desired end product. This family of compounds are based on the N-hydroxyphthalimide (BOSu) structure.

SUMMARY OF THE INVENTION

One object of the present Invention is to provide a novel family of compounds for use as agents to activate fluorescent dyes for subsequent binding to derivatized nucleotides which are used as chain terminators.

A second object of the present Invention is to provide an activated dye incorporating the activating agent of the previous object.

A third object of the present Invention is to provide a dye-labeled chain terminator incorporating the activating agent of the first object.

A fourth object of the present Invention is to provide a method for preparing an activated dye incorporating the activating agent of the first object.

A fifth object of the present Invention is to provide a method for preparing a dye-labeled chain terminator incorporating the activating agent of the first object.

A sixth of object of the present Invention is to provide a method for identifying the sequence of a nucleic acid molecule of interest comprising the steps of constructing truncated portions of a strand complementary to a nucleic of interest using the chain terminators of the previous object, and measuring the fluorescence from irradiating the dye to determine the position of the chain terminator on the truncated strand.

In accordance with one aspect of the fourth object of the present Invention, there is provided a method for preparing an activated dye incorporating the activating agent of the first object, comprising the steps of combining a suitable cyanine dye with carbonyliimidazole to form a mixture; and adding to said mixture N-hydroxyphthalimide to form a final mixture, and further wherein said dye and said carbonyliimidzazole are combined in the presence of N,N-dimethyl formamide. In accordance with another aspect of this object, said mixture is reacted for 2 hours. In accordance with still another aspect of the fourth object of the present Invention, N-hydroxyphthalimide is added to said mixture at a concentration of about 2 equivalents. In accordance with a further aspect, the method comprises the additional step of stirring said final mixture for between about 5 and about 12 hours.

In accordance with still another aspect, the method comprises the additional step of combining said final mixture with ethyl acetate. In accordance with another aspect, the method comprises the additional step of separating a resulting precipitate which comprises the desired activated dye. In accordance with a further aspect, said separating step is performed by filtration and involves the additional step of drying said isolated precipitate. In accordance with still another aspect, said dye is Cy5. In accordance with another aspect, said first combining step occurs in the presence of DMF, and said dye and said carbonyliimidazole are stirred at ambient temperature for approximately 2 hours. In accordance with still another aspect, said dye is present in said combining step at about 0.256 mmol, and said carbonyliimidazole is present in said combining step at about 0.64 mmol. In accordance with another aspect, the method comprises the additional step, subsequent to said adding step, of stirring said final mixture for between about 5 and about 12 hours. In accordance with still another aspect, the method comprises the additional step of pouring said final mixture into a solution comprising about 150 ml of ethyl acetate. In accordance with still another aspect, the method comprises the additional step of isolating a resulting solid from said final mixture by vacuum filtration. In accordance with yet another aspect, the method comprises the additional step of washing said resulting sold after vacuum filtration with ethyl acetate. In accordance with still another aspect, the method comprises the additional step of drying said resulting solid after washing by storing in a vacuum desiccator.

In accordance with one aspect of the fifth object of the present Invention, said combining step occurs in the presence of an $HCO_3^-/CO_3^{2-}$ buffer. In accordance with another aspect, said combining step occurs at room temperature for between about 1 and about 16 hours. In accordance with yet another aspect, the method comprises the additional step of isolating said chain terminator from said mixture by preparative thin-layer chromatography on silica gel using a $CHCl_2/CH_3OH$ mixture in an approximately 1:1 ratio. In accordance with still another aspect, the method comprises the additional step of further purifying said chain terminator by reverse phase high performance liquid chromatography.

Other and further objects, features, and advantages will be apparent in the following description of preferred embodiments of the Invention, given for the purpose of disclosure and taken in conjunction with the accompanying drawings.

DETAILED DESCRIPTION OF THE PREFERRED EMBODIMENT

Figure 1:
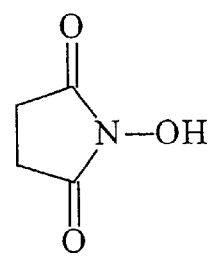
FIG. 1 shows the chemical structure of two different activating groups (top, paranitrophenol; bottom, N-hydroxysuccinimide) used to activate cyanine dyes for subsequent complexation with dideoxynucleotide-amines.
Figure 1:
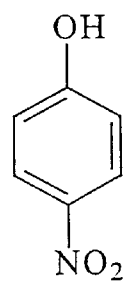
Figure 2:
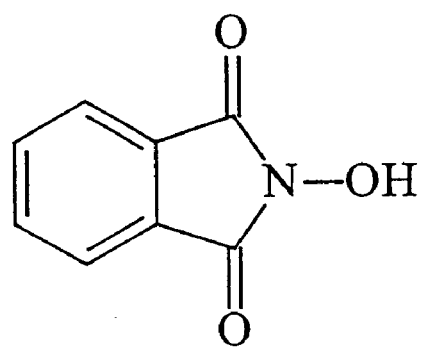
FIG. 2 shows the activating group of the present Invention.

The skilled artisan will quickly realize that various substitutions and modifications may be made to the Invention disclosed herein without departing from the scope and spirit of the invention.

The primary, though not exclusive, advantage of the activating groups of the present Invention, compared with the prior art, is that it provides greater selectivity of the mono-substituted product (e.g., Cy5-ddUTP) versus the di-substituted product (e.g., Cy5-(ddUTP)2). A second advantage of the activating groups of the present Invention is that the yield of the reaction between the dye and the chain terminator is far greater.

The present Invention relates to novel compounds and methods for preparing those compounds which can be used in nucleic acid and protein sequencing. The dideoxy chain termination method of sequencing relies upon several fluorescent dyes which are attached to the base of the dideoxy chain terminators, and act as tags. A different dye is used for each type of nucleotide base (A, T, G, or C) which allows the investigator to determine the particular nucleotide base that occurs at a particular position in the sequence, and thus, ultimately the entire sequence, by comparison of the various chain lengths and the particular tag observed at the chain's terminus.

As discussed in the Background section, specific activating compounds are used to promote the complexation of the dye to the chain terminator, i.e., first the dye is "activated," then it is reacted with the chain terminator. The point of attachment between the chain terminator and the dye occurs at the activating group. Ideally, the reaction between the chain terminator and dye occurs in a 1:1 stoichiometry; that is, a mono-substituted product is desired. Yet unintended di-substituted products frequently occur (i.e., two chain terminators bound to a single dye molecule). The present Invention addresses this along with a number of problems related to the reaction efficiency and selectivity of the activating group for the chain terminator.

Thus, the present Invention discloses a novel family of activating groups, based on the N-hydroxyphthalimide (BOSu) structure. The present Invention also discloses a novel family of activated dyes based on this novel activating group, as well as novel dye-labeled chain terminators which incorporate the novel activating group. Novel methods of synthesis for each of these three classes of compounds is also disclosed. The activating groups of the present Invention allow much higher selectivity for the mono-substituted product over the di-substituted product, and a far higher yield for the coupling reaction is observed.

Examples 1 through 3 discuss preferred methods for synthesis of cyanine dyes which, when coupled with the activating groups of the present Invention, become the novel activated dyes of the present Invention. Examples 4 and 5 show preferred methods for synthesis of two different dideoxy nucleotides, or chain terminators which, when coupled with the activating dyes of the present Invention, become the novel chain terminators of the present Invention.

Examples 6 and 7 below show preferred methods for synthesizing the activated dyes of the present Invention, which incorporate the activating groups of the present Invention. Example 8 shows a preferred method for synthesizing activated dye-labeled chain terminators, which incorporate the activated dyes of Example 7. Methods for synthesis of the activating groups of the present Invention are not disclosed herein since such methods for synthesizing such low molecular weight compounds are well known in the art. Examples 9 through 12 present experimental data which show the superior characteristics of the activating groups of the present Invention compared with those in the prior art.

EXAMPLE 1

Synthesis of DBCy5

In a dried 200 ml round bottomed flask was added 1,1,2-trimethyl-1H-benz(e)indole (11.0 g., 52.6 mmol) and a stir bar. The flask was then cooled in an ice water bath. Sulfuric acid (10 ml) was added and stirred to partially dissolve the solid. Oleum (25 g, 30% SO$_3$,~93.7 mmol) was added and stirred at 0° C. for 30 min and then room temperature overnight with the exclusion of moisture. The acid oil was then poured into ice (200 ml) and stirred for 30 min. The acid solution was then neutralized with potassium hydroxide untile basic (pH>12). The dried solid was then extracted with hot methanol (~11). The undissolved salt was filtered off and the filtrate was concentrated to a solid, triturated with EtOAc (300 ml) and the solid was collected, washed with EtOAc (2×50 ml) and dried. Further drying in an oven at 45° C. under high vacuum provided 17 g (quantitative) of the product, potassium 1,1,2-trimethylbenzoindolenine-7-sulfonate (TLC:R$_f$=0.28(4:1 CH$_2$Cl$_2$:MeOH)).

A mixture of potassium 1,1,2-trimethylbenzoindolenine-7-sulfonate (10.00 g, 30.54 mmol), bromohexanoic acid (7.74 g, 39.7 mmol) in 1,2-dichlorobenzene (100 ml) was heated in a 250 ml round bottomed flask in an oil bath at 120° C. for 48 h until all starting material was consumed. The reaction was followed by TLC (1:1 CH$_2$Cl$_2$:MeOH) for the disappearance of starting material (R$_f$=0.88) and formation of the product, 1-(carboxypentyl)-2,3,3- trimethylbenzoindolenine-7-sulfonate ($R_f$=0.30). After cooling to room temperature, solvent was decanted and washed with EtOAc (2×20 ml). The solid was then triturated when deionized water (50 ml), collected through filtration and washed with a small amount of methanol. After drying in an oven at 40° C. under high vacuum overnight, 10.3 g (83%) of a grey solid product was obtained.

A mixture of 1.88 g, 4.66 mmol), potassium acetate (229 mg, 2.33 mmol) and methanol (20 ml) in a 100 ml round bottomed flask was heated in an oil bath at 70° C. for 30 min with the exclusion of moisture. Trimethoxypropene was added (0.6 ml per 30 min) and refluxed for a total of 1 h. KOAc was filtered off through a pad of paper and rinsed with MeOH (3×5 ml). The filtrate was then poured into EtOAc (400 ml) in a beaker. The resultant solid was collected through filtration, washed with EtOAc:MeOH (1:9, 3×50 ml) and then EtOAc (2×50 ml). After drying in an oven at 40° C. under high vacuum overnight, 1.51 g (74%) of a blue solid, DBCy5 was obtained. TLC: $R_f$=0.33 (1:1 $CH_2Cl_2$:MeOH), UV ($\lambda_{max}$=684 nm in MeOH).

EXAMPLE 2

Synthesis of Cy7

Sodium glutaconaldehyde was prepared in a 500 ml three-necked round bottomed flask equipped with a mechanical stirrer. Sodium hydroxide (42 g, 1.05 mol) and water (168 ml) were added to the flask and then cooled to −30° C. with an acetone-dry ice bath for 30 min. Pyridinium 1-sulfonate (48 g, 0.3 mol), which had been previously chilled to −20° C., was added in one portion. The mixture was stirred for 20 min at about −20° C. to −5° C. The cooling bath was removed and replaced with a water bath at room temperature. After stirring for 20 min, the bath was heated to about 55° C. to 60° C. and stirred for 1 h. The color of the mixture turned from yellow to dark brown. The mixture was then recooled to −5° C. The solid was collected through filtration, washed with acetone (3×100 ml) and dried in an oven at 50° C. under high vacuum overnight. A 62% yield of solid sodium gluconaldehyde (29.0 g) was obtained. UV ($\lambda_{max}$=362 nm in MeOH).

A dried 100 ml round bottomed flask containing acetic anhydride (30 ml) was heated to reflux using an oil bath. The oil bath was removed. 1-(Carboxypentyl)-2,3,3-trimethylindoleninium-5-sulfonate (3.0 g, 8.49 mmol) and sodium gluconaldehyde (663 mg, 4.25 mmol) were then added in one portion. The color of the mixture turned blue almost instantly. The reaction was stirred at ambient temperature for 1 h, poured into a 1 l beaker with EtOAc (500 ml), and rinsed with MeOH (15 ml). The resultant solid was collected, washed with EtOAc (3×50 ml), and dried in a desiccator. Further drying in an oven at 30° C. under high vacuum overnight gave a final yield of 2.654 g (79%) of dark blue Cy7 solid. An activated ester of Cy7, Cy7-N-hydroxyphthalimide (DBCy5(BOSu)$_2$), was prepared by a procedure similar to Example 1 by substituting Cy7 in the esterification reaction.

EXAMPLE 3

Synthesis of DBCy7

1-(carboxypentyl)-2,3,3-trimethylbenzo-indolenine-7-sulfonate was prepared according to methods known in the art. A solution of the benzoindole sulfonate (500 mg, 1.24 mmol) and sodium gluconaldehyde (96.7 mg, 0.619 mmol) in acetic anhydride (5 ml) was heated in a test tube using a heat gun to reflux for 2 min. The color of the solution turned dark green (TLC(1:1 $CH_2Cl_2$:MeOH)) showed primariy one spot of product together with some starting material. The crude mixture was then poured into EtOAc (100 ml) and filtered to remove the unreacted starting material. The filtrate was concentrated to a small volume and mixed with EtOAc (100 ml). The resultant solid was collected, washed with EtOAc and dried. A 66% yield of dark green DBCy7 solid (363 mg) was obtained. An activated ester of DBCy7, DBCy7-N-hydroxyphthalimide (DBCy7(BOSu)$_2$), was prepared by a procedure similar to Example 7, below, simply by substituting DBCy7 in the esterification reaction.

EXAMPLE 4

Synthesis of 2',3'-Dideoxyuridine (ddU)

A. Preparation of 5-Iodo-2',3'-dideoxyuridine (1)

Iodine (1.786 g, 6.91 mmol), silver nitrate (1.96 g, 6.29 mmol) and methanol (60 mL) were added to a dry 250 mL round bottom flask and stirred for 1 min under a nitrogen atmosphere. Into the above mixture was added dideoxyuridine (1.334 g, 6.29 mmol) and stirring continued at room temperature under a nitrogen atmosphere for 5 h. Then layer chromatography analysis showed only a trace of the starting material remained unreacted indicating the completion of the reaction. The solid was filtered off and the filtrate was concentrated to dryness. The residue was dissolved in methanol and preadsorbed on silica gel which was chromatographed on a silica gel column using gradient methylene chloride and methanol (up to 30 v/v %). The fractions containing the product were combined and the solvent was evaporated off to give a solid, which was then recrystallized from a mixture of methanol and diethylether. The solid was filtered and dried at 40° C. to obtain 1.093 g (51.4% yield) of product. Silica gel thin layer chromatography showed an $R_f$ of 0.61 in 9:1 dichloromethane:methanol eluant.

$^1$H NMR (300 MHZ): (DMSO-d6) δ1.8–2.4 (4H, $H_{2'}$ and $H_{3'}$). 3.53 and 3.75 (2H, $2H_{5'}$, two m), 4.06 (1H, $H_{4'}$, m), 5.23 (1H, 5'OH, br s), 5.92 (1H, $H_{1'}$, dd, J=6.6 Hz, 2.7 Hz), 8.62 (1H, $H_6$, s), 11.65 (1H, NH, br s).

B. Preparation of 5-(3-Trifluoroacetamido-1-propynyl)-2',3'-dideoxy-uridine (2)

"Iodo-ddU" (338 mg, 1.0 mmol), cuprous iodide (38.1 mg, 0.2 mmol) and DMF (5 mL) were added into a 250 mL round bottom flask under a nitrogen atmosphere. While stirring, the following reactants were added to the above reaction mixture; N-propargyltrifluoroacetamide (0.35 mL, 3.0 mmol), triethylamine (0.28 mL, 2 mmol) and tetralis (triphenylphosphine)palladium(O) (115 mg, 0.1 mmol). The reaction mixture was stirred at room temperature for 3.5 h. Thin layer chromatography on the reaction mixture showed completion of the reaction. Solvent was evaporated off under reduced pressure and the residue was dissolved in methanol, which was absorbed on silica gel for column chromatography. The silica gel absorbed sample was loaded on a silica gel column and eluted with dichloromethane containing zero to 10 v/v % methanol. Fractions containing the product were combined and the solvent was evaporated to dryness to obtain 305 mg (84.5%) of product. Thin layer chromatography analysis showed a single spot on a silica gel plate with eluant 9:1 dichloromethane:methanol having an $R_f$ of 0.57.

$_1$H NMR (300 MHZ): (CDCl$_3$) δ1.8–2.4 (4H, $H_{2'}$ and $H_{3'}$, m), 3.90 and 4.10(2H, $2H_{5'}$, two m), 4.25 (1H, $H_{4'}$, m), 4.32 (2H, propargyl CH, d, J=4 Hz), 6.08 (1H, $H_{1'}$, dd, J=6.6 Hz, 2.7 Hz), 8.22 (1H, NHTFA, br s), 8.32 (1H, $H_6$, s), 9.51 (1H, NH, br s).

EXAMPLE 5

Synthesis of 2'-3'-Dideoxycytidine (ddC)

A. Preparation of 5-Iodo-2',3'-dideoxycytidine (1)

A solution of 2',3'-dideoxycytidine (500 mg, 2.36 mmol), and mercuric acetate (800 mg, 2.5 mmol) in methanol (25 mL) was refluxed for 10 h. The white suspension was diluted with methanol (15 mL) in dichloromethane (25 mL). Iodine (750 mg, 2.95 mmol) was added and the suspension was stirred at room temperature until a clear purple solution resulted (in about 4 h). The free base form of AG 3X4A resin (3.5 g, Bio-Rad, a weakly basic polystyrene resin) was added and hydrogen sulfide was bubbled into the reaction mixture for 10 min. The reaction mixture was filtered through a filter aid, which was washed with 1:1 methanol and dichloromethane. The filtrate was concentrated and the resultant solid was collected through filtration, washed with diethyl ether, and dried to give 670 mg of pure product (85.8%). The $R_f$ on a silica gel plate using 10% methanol in dichloromediane was 0.2.

$^1$H NMR (DMSO-$d_6$); 1.79–2.3 (m, 4H, $H_{2''}$ and $H_{3'}$,), 3.5 5(dt, 1H, $H_{5''}$, b), 3.73 (dd, 1H, $H_{5''}$, a), 4.05 (m, 1H, $H_{4''}$), 5.2 (t, 1H, 5"—OH), 5.86 (dd, 1H, $H_{1''}$), 6.55 (broad s, 1H, $NH_2$b), 7.75 (broad s, 1H, $NH_2$a) and 8.5 (s, 1H, $H_6$).

B. Preparation of 5-(3-Trifluoroacetamido-1-propargyl)-2',3'-dideoxycytidine (2)

A 50 mL flask was charged with iodocytidine (350 mg, 1 mmol) and cuprous iodide (3.81 mg, 0.2 mmol). After flushing the flask with argon, dry N,N-dimethylformamide (5 mL) was added, followed by triethylamine (0.28 mL, 4.0 mmol), N-propargyltrifluoroacetamide (0.35 mL, 3.0 mmol), and tetrakis(triphenylphosphine)palladium (0) (115.5 mg, 0.1 mmol). The reaction mixture was stirred overnight. Methanol (10 mL) was added the reaction mixture was evaporated at 45° C. The residue was immediately purified by column chromatography using 50 g silica gel and 5%, 10%, and then 15% v/v methanol in dichloromethane. The fractions containing pure product were pooled and evaporated to dryness to obtain 350 mg (93.6%) of product as a beige foam. The $R_f$ on a silica gel plate using 15% v/v methanol in dichloromethane is 0.58.

$_1$H NMR (DMSO-$d_6$); 1.8–2.3 (m, 4H, $H_{2''}$ and $H_{3''}$), 3.5 (dt, 1H, H5", b), 3.7 (d, 1H, $H_{5''}$, a), 4.1 (m 1H, $H_{4''}$), 4.3 (d, 2H, $CH_2$), 5.18 (t, 1H, 5"-OH), 5.9 (dd, 1H, $H_{1''}$), 6.8 (broad s, 1H, $NH_2$b), 7.8 (broad s, 1H, $NH_2$a), 8.35 (s, 1H, $H_6$) and 10.0 (broad s, 1H, NH-Triflate). UV (methanol: $\lambda_{max}$ 232 and 294 nm.

EXAMPLE 6

Synthesis of Activated Dyes

Figure 3:
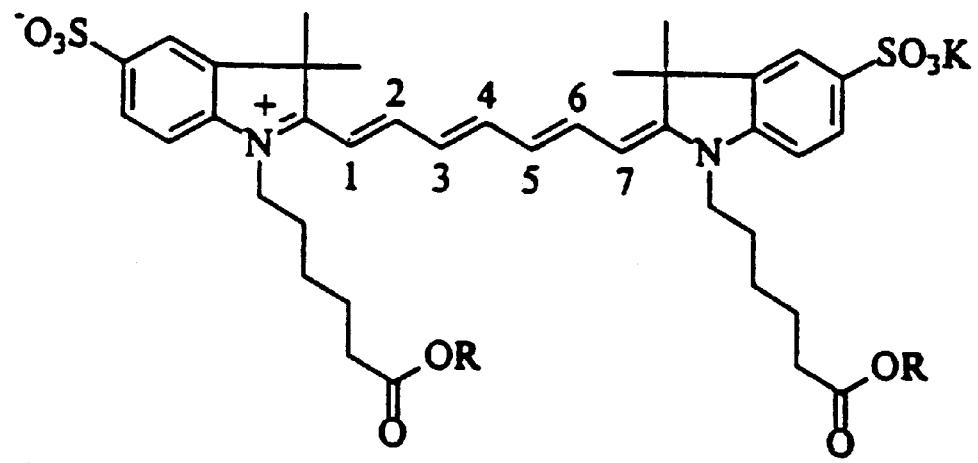
FIG. 3 shows four different cyanine dyes of the present Invention, prior to addition of the activating group, which is attached at the "R" position. The following nomenclature shall be used herein (beginning with the dye shown at the upper left-hand corner and proceeding clockwise) Cy5, Cy7, DBCy5, and DBCy7.
Figure 3:
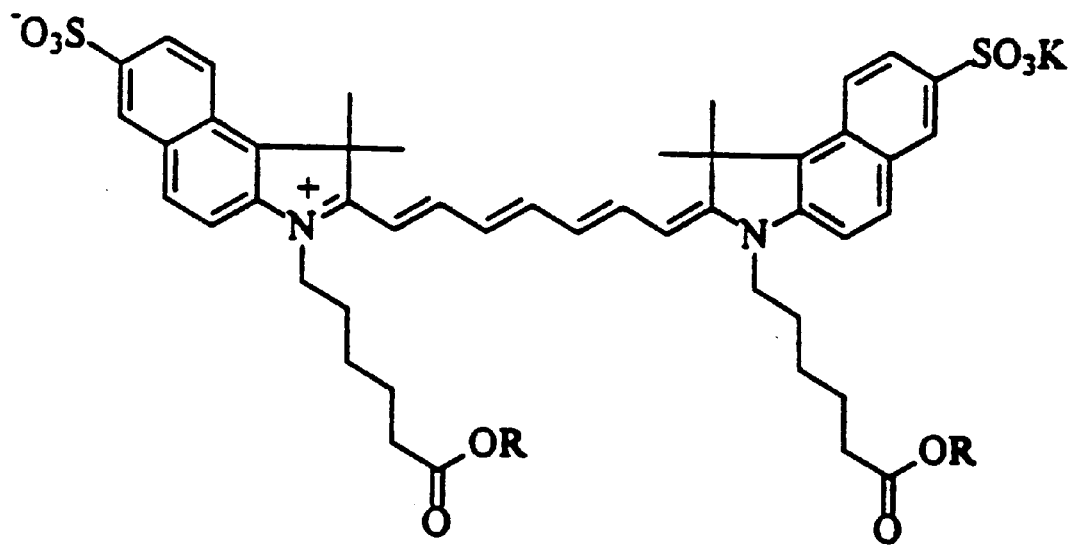
Figure 3:
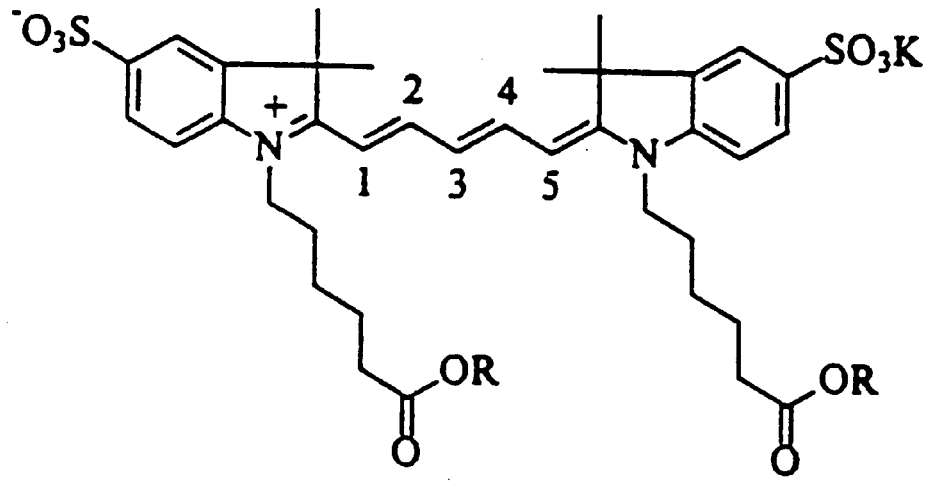
Figure 3:
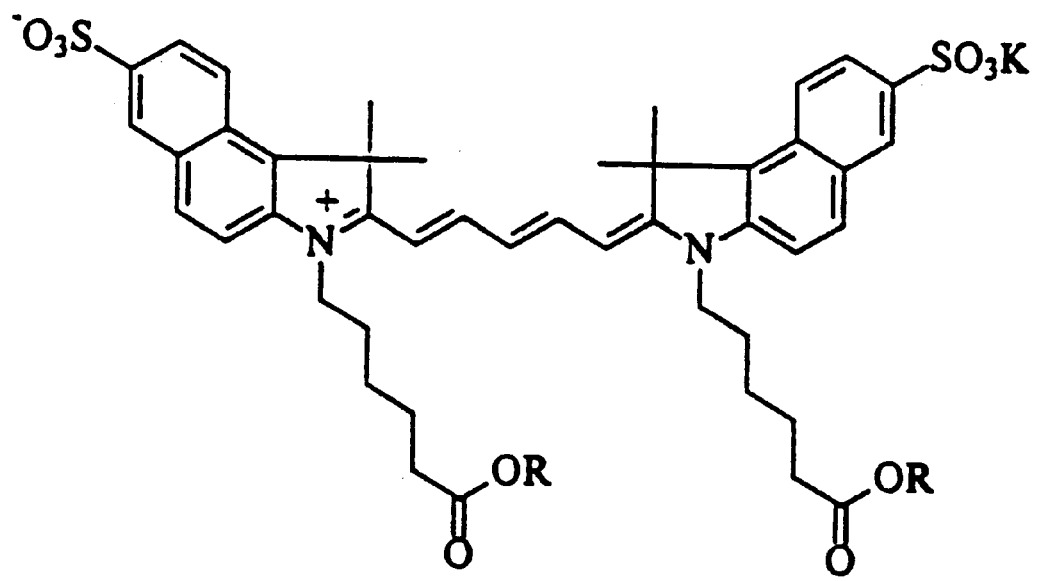

This example describes a preferred means for the preparation of activated dyes incorporating the activating group of the present Invention. First, a suitable dye, such as the cyanine dyes shown in FIG. 3 are contacted with carbonyldiimidazole in N,N-dimethylformamide for two hours. To this mixture is added 2.2 equivalents of N-hydroxyphthalimide (BOSu). This three-component solution is stirred for approximately 10 hours, then poured into a solution of ethyl acetate. The desired product will form a precipitate, which can then be isolated by filtration then dried to yield the activated dye. A more detailed method is discussed in the next Example.

EXAMPLE 7

Synthesis of an Activated Ester of Cy5

To a 500 ml round bottomed flask equipped with a stir bar and reflux condenser was added AcOH (150 ml), p-hydrazinobenzenesulfonic acid (50.0 g, 0.255 mol), and 3-methyl-2-butanone (84 ml, 0.785 mmol). The flask was then heated in an oil bath at 115° C. to reflux for 3 h until all the starting material consumed (monitored by TLC, 1:1 MeOH:$CH_2Cl_2$). The oil bath was removed and the flask was cooled to room temperature. The pink solid was collected via filtration with the acid of EtOAc. The solid was then dissolved in MeOH (800 ml) and air dried. Further drying in an oven at 40° C. under high vacuum overnight provided 64.5 g (87.5%) of the desired product, 2,3,3-trimethylindoleninium-5-sulfonate, potassium salt. TLC: $R_f$=0.875 (1:1 $CH_2Cl_2$:MeOH).

A mixture of the potassium indole sulfonate (15.25 g, 55.0 mmol), bromohexanoic acid (13.4 g, 68.7 mmol) in 1,2-dichlorobenzene (140 ml) in a 250 ml round bottomed flask was heated in an oil bath at 110° C. under nitrogen for 24 h. After cooling to room temperature, solvent was decanted and the solid was triturated with 2-isopropanol (200 ml). The solid was collected through filtration, washed with EtOAc (3×100 ml) and dried in an oven at 40° C. under high vacuum overnight to give 15.9 g (83.3%) of the product, 1-(carboxypentyl)-2,3,3-trimethylindoleninium-5-sulfonate TLC: $R_f$=0.80 (1:1 $CH_2Cl_2$:MeOH)).

A mixture of 1-(carboxypentyl)-2,3,3-trimethylindoleninium-5-sulfonate (5.22 g, 14.8 mmol), potassiium acetate (725 mg, 7.39 mmol) and methanol (40 ml) in a 100 ml round bottomed flask was heated in an oil bath at 70° C. for 30 min under nitrogen atmosphere. Trimethoxypropene (4 ml, 1 ml per 20 min) was added and refluxed for a total of 2 h. The potassium acetate was filtered off through a pad of paper and the filtrate was rinsed with MeOH. The filtrate was concentrated to dryness and redissolved in MeOH (10 ml). Isopropanol (150 ml) was added and the resultant solid was stirred and collected through filtration. The collected solid was washed with isopropanol (2×30 ml), then EtOAc (3×30 ml), and finally with ether (2×20 ml). After drying in an oven at 40° C. under high vacuum overnight, 5.03 g (87.2%) of a blue solid Cy5, was obtained. TLC: $R_f$=0.31 (1:1 $CH_2Cl_2$:MeOH).

Carbonylimidazole, CDl, (104 mg, 0.64 mmol) was added to a solution of Cy5 (200 mg, 0.256 mmol) in DMF (10 ml), under nitrogen atmosphere and shielded from light. The reaction was stirred at ambient temperature for 2 h. N-hydroxiphthalimide (104 mg, 0.64 mmol) was added and the reaction was stirred overnight. The mixture was poured into ethyl acetate (150 ml) and the resultant solid was collected by vacuum filtration, washed with ethyl acetate (2×10 ml), and dried in a vacuum desiccator to give Cy5-n-hydroxyphthalimide (Cy5($BOSu)_2$, 200 mg, 0.209)), a dark blue solid.

EXAMPLE 8

Synthesis of Dye-Labeled Chain Terminators

Figure 4:
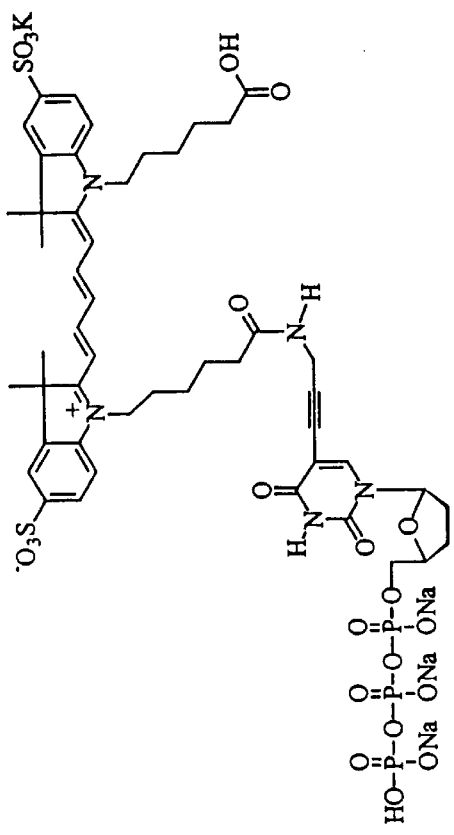
FIG. 4 shows two different dye-labeled chain terminators. On top is a mono-substituted chain terminator, Cy5-Mono-ddUTP; on the bottom is a di-substituted analog. Both chain terminators consist of a dideoxynucleotide triphosphate portion and a cyanine dye portion, joined by reaction with activating group of the present Invention.
Figure 4:
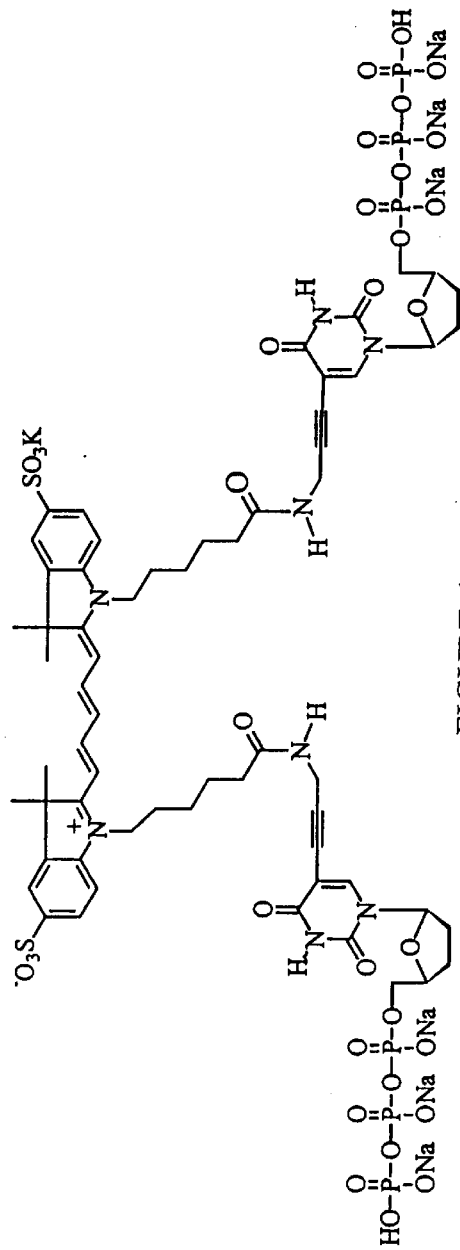

This example describes the preparation of dye-labeled chain terminators, such as those shown in FIG. 4. The necessary reagents are a cyanine dye, an activating group, and a dideoxynucleotide triphosphate. This three-component complex shall be referred to as ddNTP-CyX. The dye is reacted with the activating group, preferably following the directions in Example 1 above, to form an activated dye, which can then react with the nucleotide with enhanced selectivity for the mono-substituted product. In a preferred synthesis, the activated dye (CyX(ACT) is added to the ddNTP-PA in the presence of a carbonate buffer, at room temperature for between 1 to 16 hours. The reaction mixture is then crudely purified by preparative thin-layer chromatography on silica gel using $CH_2Cl_2/CH_3OH$ in a 1:1 ratio. The band at the origin represents the desired product. Finally, the ddyNTP-CyX is preferably purified further by reverse phase high-performance liquid chromatography (HPLC).

EXAMPLE 9

Comparison of Selectivity for Mono-Substituted Product Among Several Activating Compounds, Using Cy5-Activated Dyes This example illustrates the superior selectivity of mono-substituted over di-substituted products achieved using the activating group of the present Invention. To show this, 5-(3-amino-1-propynyl)-2"-dideoxyuridine (ddUTP-PA) was reacted with three different activated dyes: $Cy5(BOSu)_2$ of the present Invention, $Cy5(NHS)_2$, and $Cy5(pNP)_2$, the latter two from the prior art. The comparison was based on the CE of the bottom band of preparative thin-layer chromatography (TLC). The CE were run on a Beckman P/ACE 550 using a 25µ×27 cm bare fused silica capillary at 20 k volts and 23 µA in 100 mM borate buffer at pH 10.2.

Figure 5:
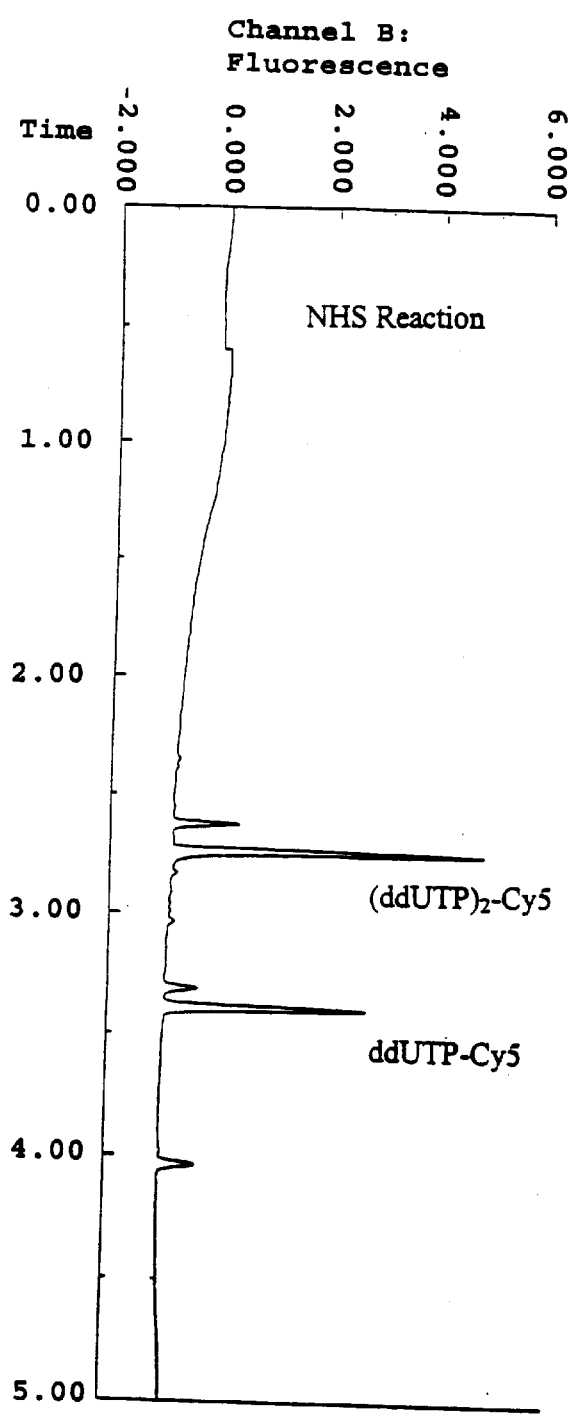
FIG. 5 shows two elution profiles from thin-layer chromatography, obtained by passing the reaction products of the reaction between 5-3-amino-1-propynyl)-2"-dideoxyuridine and Cy5(BOSu)$_2$ (FIG. 5a) or Cy5(NHS)$_2$ (FIG. 5b) through a fused-silica capillary. Thus, FIG. 5 allows comparison of the selectivity (between mono- and di-substituted products) for a prior art activating group against the activating group of the present Invention.
Figure 5:
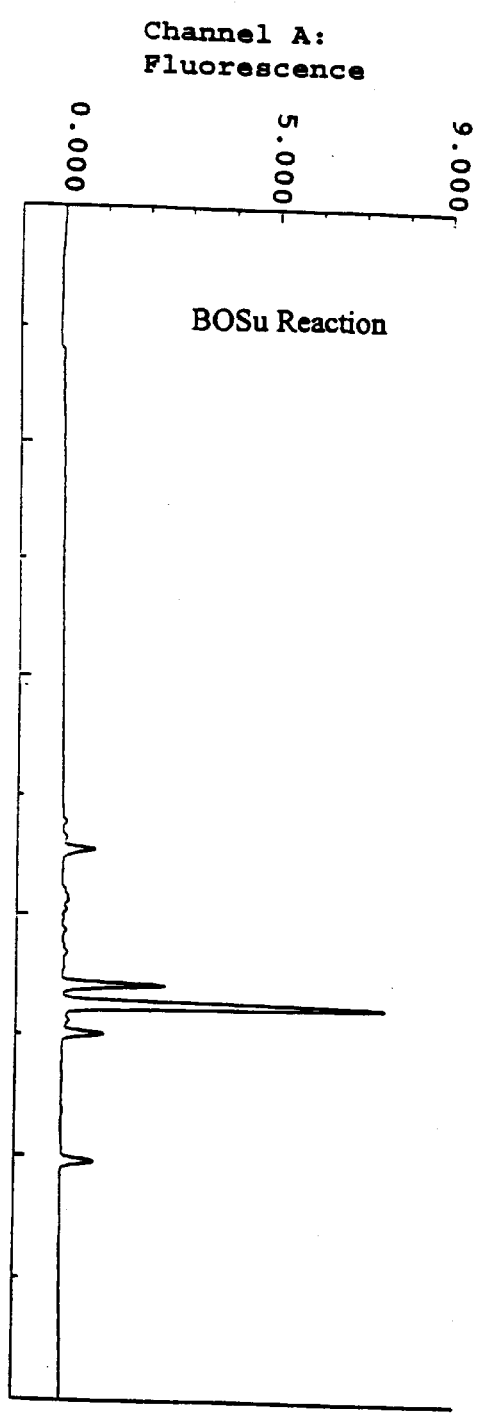
Figure 6:
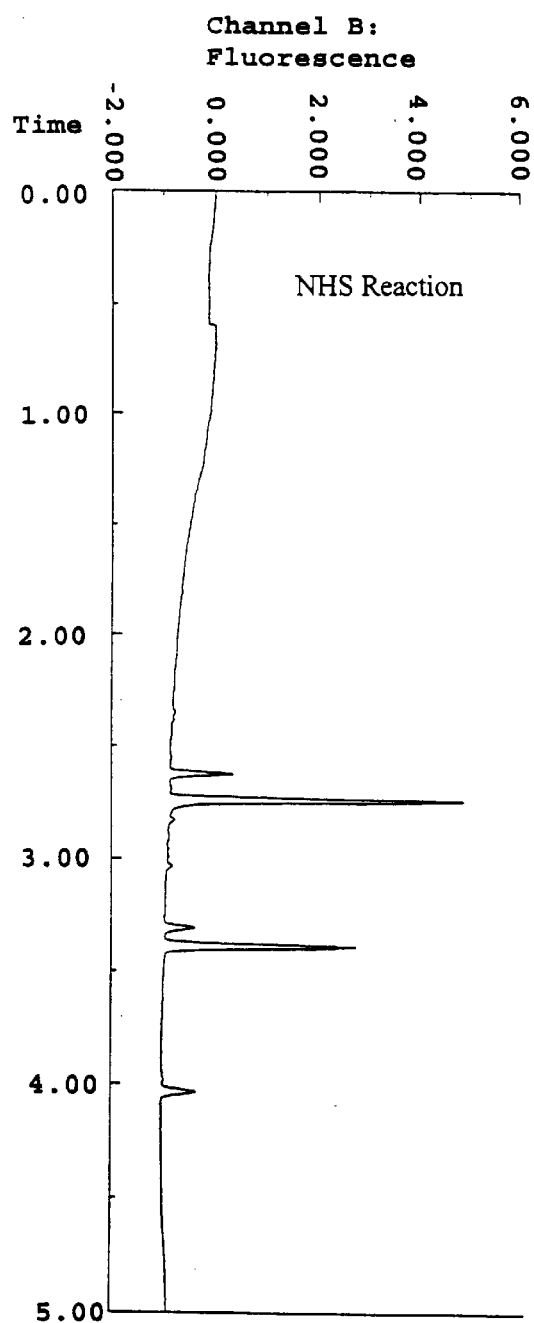
FIG. 6 shows two elution profiles, from thin-layer chromatography, obtained by passing the reaction products of the reaction between 5-3-amino-1-propynyl)-2"-dideoxyuridine and Cy5(pNP)$_2$ (FIG. 6a) pr Cy5(NHS)$_2$ (FIG. 6b) through a fused-silica capillary. Thus, FIG. 6 in combination with FIG. 5 allows comparison of the selectivity (between mono- and di-substituted products) for two prior art activating groups against the activating group of the present Invention.
Figure 6:
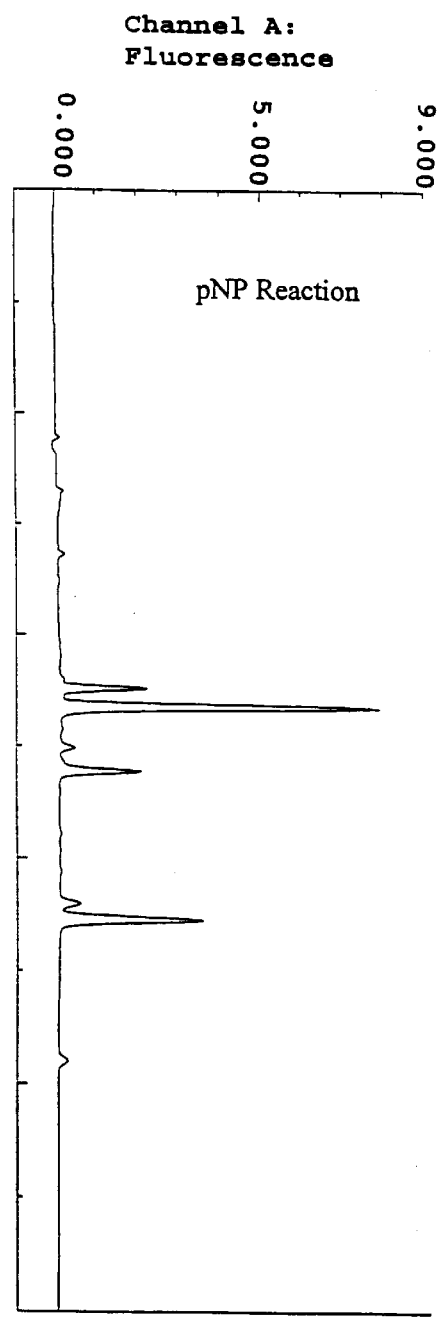

The elution profiles are shown in FIGS. 5 and 6. FIG. 5 shows two elution profiles from thin-layer chromatography, obtained by passing the reaction products of the reaction between 5-3-amino-1-propynyl)-2"-dideoxyuridine and Cy5 $(BOSu)_2$ (FIG. 5a) or $Cy5(NHS)_2$ (FIG. 5b) or $Cy5(pNP)_2$ through a fused-silica capillary. Thus, FIG. 5 allows comparison of the selectivity (between mono- and di-substituted products) for a prior art activating group against the activating group of the present Invention. As evidenced by FIG. 5a, the elution profile for BOSu, the activating group of the present Invention, shows one major peak which corresponds to the mono-substituted product (ddUTP-Cy5) at about 3.4. By contrast, FIG. 5b, the elution profile for NHS, an activating group of the prior art, shows two major peaks, which correspond to the mono-substituted ddUTP-Cy5 (at 3.4) and the di-substituted $(ddUTP)_2$-Cy5, at 2.8.

These results are corroborated by those depicted in FIG. 6. FIG. 6 shows two elution profiles, from thin-layer chromatography, obtained by passing the reaction products of the reaction between 5-3-amino-1-propynl)-2"-dideoxyuridine and $Cy5(pNP)_2$ (FIG. 6a) pr $Cy5(NHS)_2$ (FIG. 6b) through a fused-silica capillary. As in FIG. 5b, both FIGS. 6a and 6b show two significant peaks, again corresponding to the mono- and di-substituted products. Thus, FIG. 6 in combination with FIG. 5 allows comparison of the selectivity (between mono- and di-substituted products) for two prior art activating groups against the activating group of the present Invention.

EXAMPLE 10

Reaction of 5-(3-amino-1-propynyl)-2"-dideoxyuridine with $Cy7(BOSu)_2$

The remaining examples illustrate the purification steps of the reaction forming selected dye-labeled chain terminators of the present Invention. In Examples 4 through 6, a single dideoxynucleotide is reacted with a different activated cyanine dye. The resulting product is purified by TLC; the elution profile is shown as the top-most profile for each figure that corresponds to a particular example. Next, the product is further purified by reverse phase high performance liquid chromatograhy; this elution profile is shown as the bottom-most figure in each figure that corresponds that the particular example.

Figure 7:
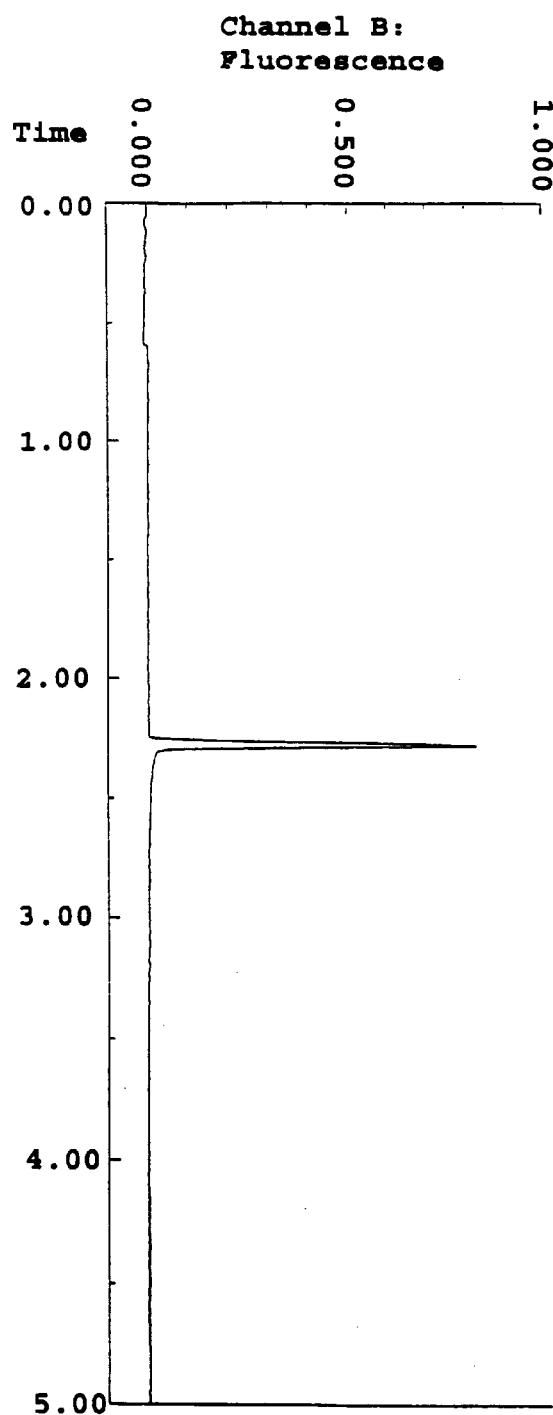
FIG. 7 shows an elution profie (FIG. 7a) from preparative thin-layer chromatography of the reaction products of 5-(3-amino-1-propynyl)-2"-dideoxycytidine and Cy7(BOSu)$_2$. The eluent was then passed through an HPLC; the resulting elution profile is depicted in FIG. 7b.
Figure 7:
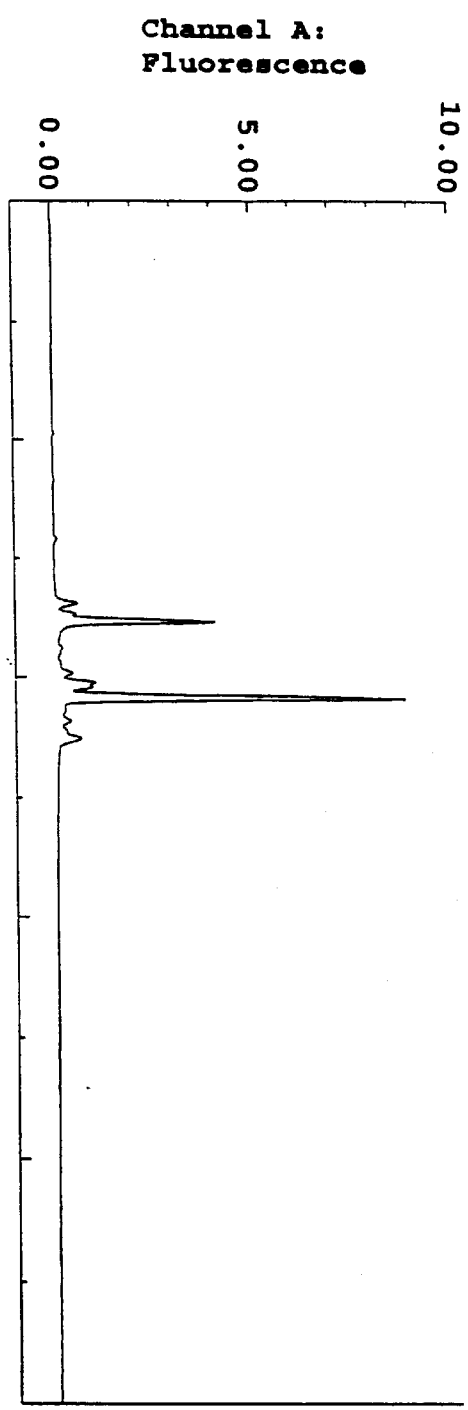

FIG. 7 shows an elution profile (FIG. 7a) from preparative thin-layer chromatography of the reaction products of 5-(3-amino-1-propynyl)-2"-dideoxycytidine and $Cy7(BOSu)_2$. The CE of the residue isolated at the origin of the preparative TLC exhibits a single main peak at 2.95 min, ddCTP-Cy-7, and five minor bands whose quantity is approximately 20% of the main peak. The elucent was then passed through an HPLC for further purification and identification; the resulting elution profile is depicted in FIG. 7b.

EXAMPLE 11

Reaction of 5-(3-amino-1-propynyl)-2"-dideoxyguanosine with $DBCy5(BOSu)_2$

Figure 8:
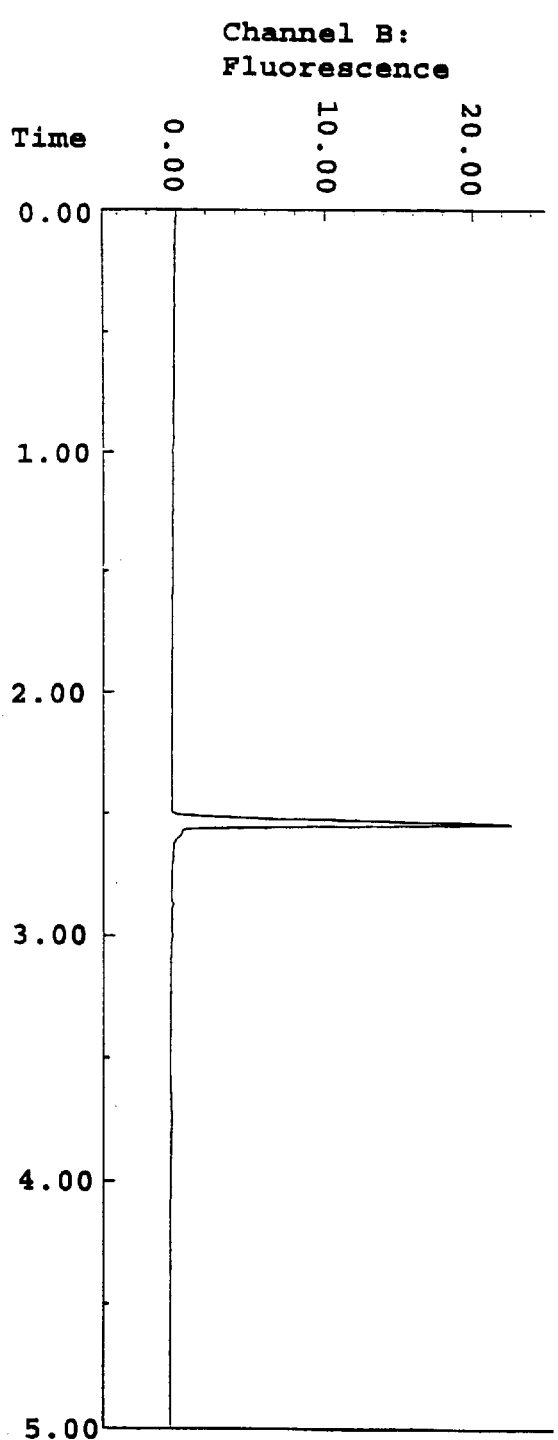
FIG. 8 shows an elution profile (FIG. 8a) from preparative thin-layer chromatography of the reaction products of 5-(3-amino-1-propynl)-2"-dideoxyguanosine and DBCy7(BOSu)$_2$. The eluent was then passed through an HPLC; the resulting elution profile is depicted in FIG. 8b.
Figure 8:
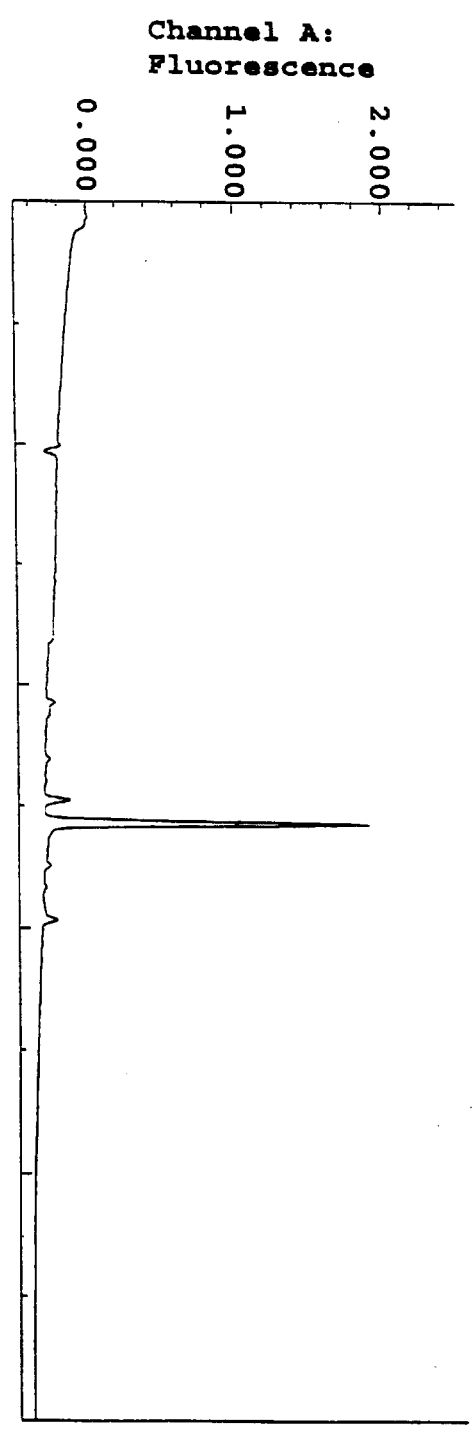

FIG. 8 shows an elution profile (FIG. 8a) from preparative thin-layer chromatography of the reaction products of 5-(3-amino-1-propynyl)-2"-dideoxyguanosine and DBCy7 $(BOSu)_2$. The CE of the residue isolated at the origin of the preparative TLC exhibits a single main peak at 2.8 min, ddCTP-Cy7 and three minor bands whose quantity is approximately 25% of the main peak. The eluent was then passed through an HPLC for further purification and identification; the resulting elution profile is depicted in FIG. 8b.

EXAMPLE 12

Reaction of 5-(3-amino-1-propynyl)-2"-dideoxyadenosine with $DBCy7(BOSu)_2$

Figure 9:
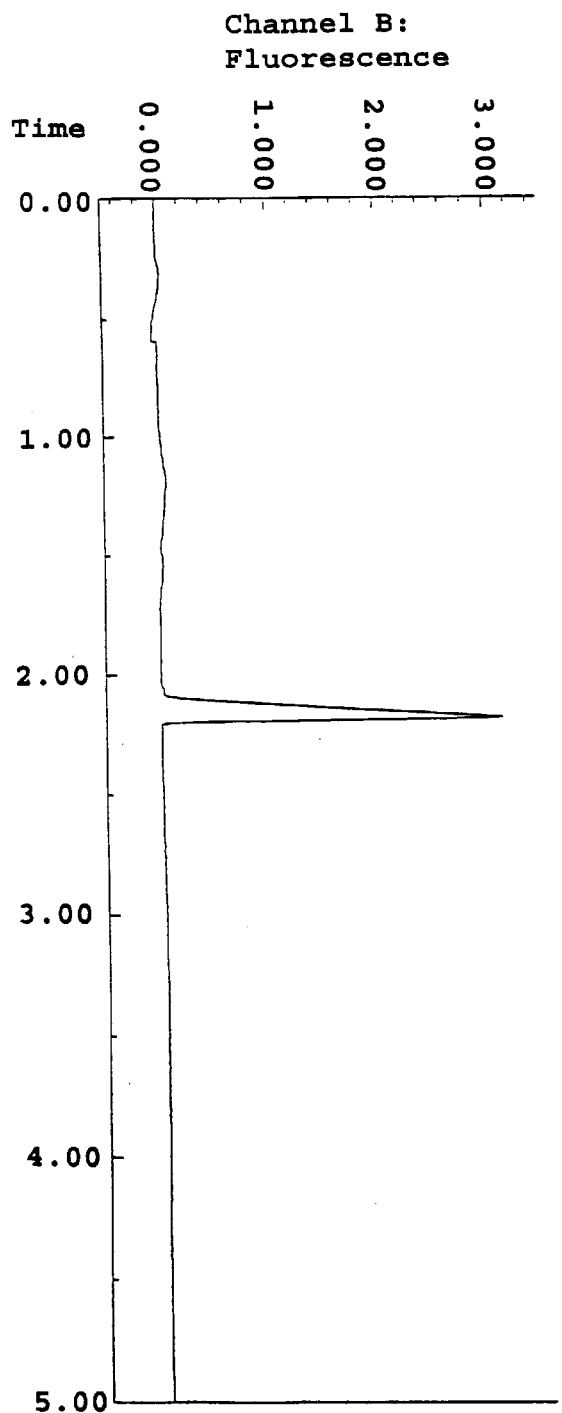
FIG. 9 shows an elution profile (FIG. 9a) from preparative thin-layer chromatography of the reaction products of 5-(3-amino-1-propynl)-2"-dideoxyadenosine and DBCy7(BOSu)$_2$. The eluent was then passed through an HPLC; the resulting elution profile is depicted in FIG. 9b.
Figure 9:
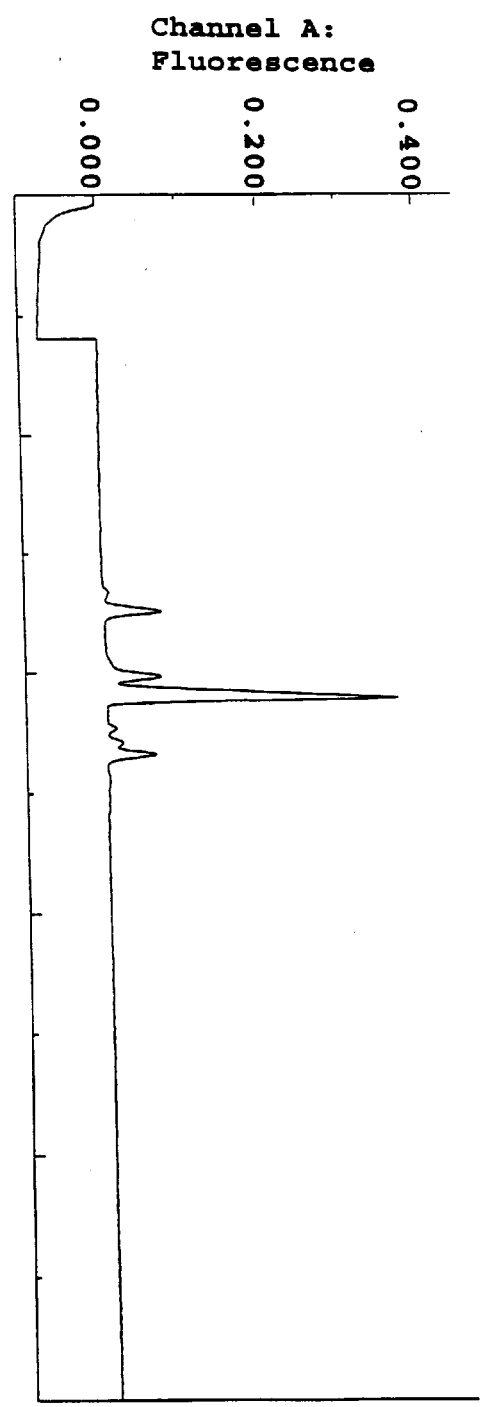

FIG. 9 shows an elution profile (FIG. 9a) from preparative thin-layer chromatography of the reaction products of 5-(3-amino-1-propynyl)-2"-dideoxyadenosine and DBCy7 $(BOSu)_2$. The CE of the residue isolated at the origin of the preparative TLC exhibits a single main peak at 3.25 min, ddCTP-Cy7 and three minor bands whose quantity is approximately 35% of the main peak. The eluent was then passed through an HPLC for further purification and identification; the resulting elution profile is depicted in FIG. 9b.

The skilled artisan will readily appreciate that the present Invention is well adapted to carry out the objects and to obtain the ends and advantages mentioned, as well as those inherent in the Invention. The compounds and methods described herein are representative of the preferred embodiments, are intended to be exemplary, and not intended as limitations on the invention scope. Additional embodiment of the Invention not described herein, but within the spirit of the invention, will occur to the skilled artisan, yet are fully encompassed by the scope of the claims.

What is claimed is:

1. An activated dye having the formula:

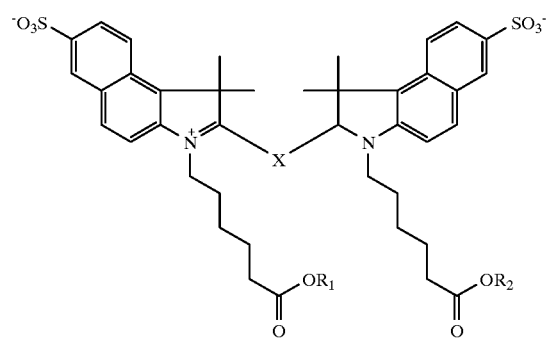

wherein X is selected from the group consisting of —CH═CH—CH═CH—CH═, and —CH═CH—CH═CH—CH═CH—CH═; and wherein $R_1$ is

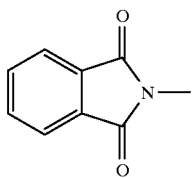

or —H; and
wherein $R_2$ is

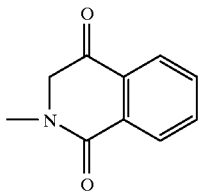

or —H; and
further wherein $R_1$ and $R_2$ are not both —H.

2. An activated dye having the formula:

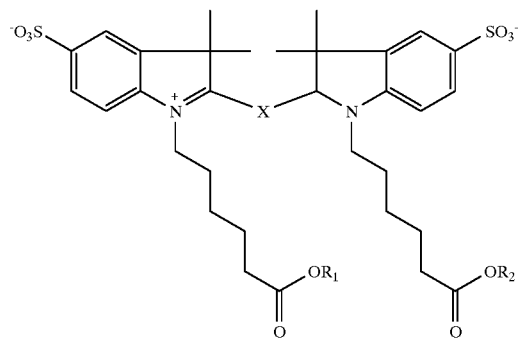

wherein X is selected from the group consisting of —CH=CH—CH=CH—CH=, and —CH=CH—CH=CH—CH=CH—CH=; and
wherein $R_1$ is

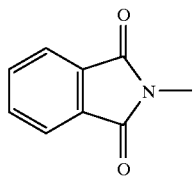

or —H; and
wherein $R_2$ is

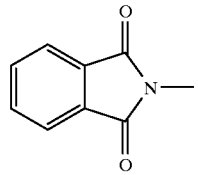

or —H; and
further wherein $R_1$ and $R_2$ are not both —H.

3. A dye-labeled chain terminator having the formula:

A—X—B wherein A is a cyanine dye selected from the group consisting of

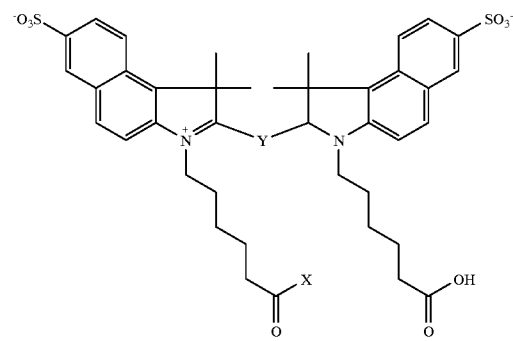

, and

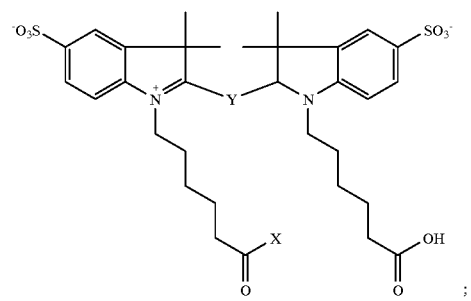

;

wherein Y is selected from the group consisting of —CH=CH—CH=CH—CH=, and —CH=CH—CH=CH—CH=CH—CH=; and
wherein B is selected from the group consisting of

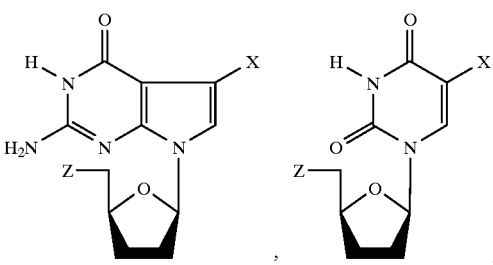

, and

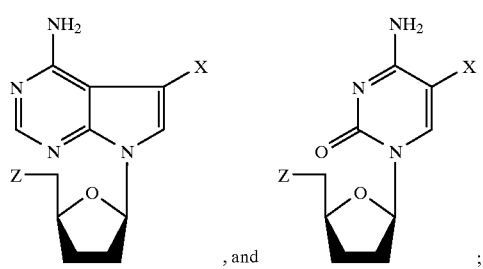

;

wherein Z is

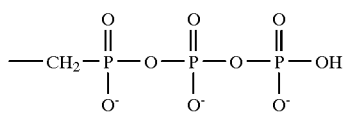

and wherein X is a linking group that results from reacting A and N-hydroxyphthalimide to produce an activated dye; and thereafter reacting said activated dye with B.

4. A method for preparing an activated dye having a formula selected from the group consisting of:

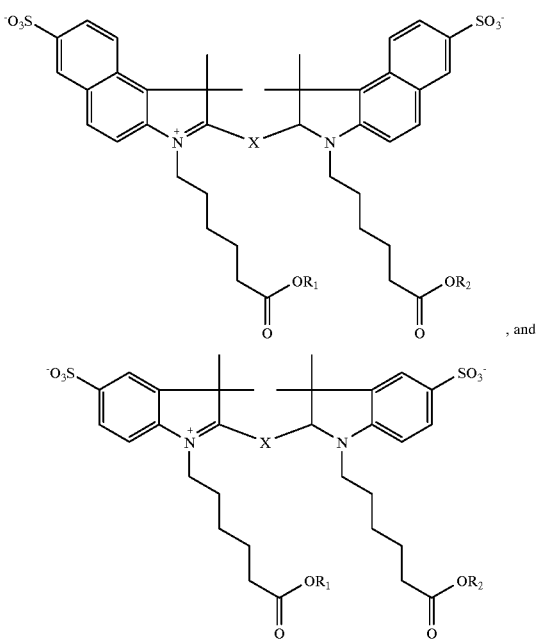

wherein X is selected from the group consisting of —CH=CH—CH=CH—CH=, and —CH=CH—CH=CH—CH=CH—CH=; and wherein $R_1$ is

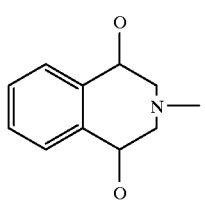

or —H; and
wherein $R_2$ is

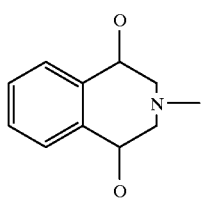

or —H; and further wherein $R_1$ and $R_2$ are not both —H;

which comprises:

combining a suitable cyanine dye with carbonyliimidazole to form a mixture; and adding to said mixture N-hydroxyphthalimide to form a final mixture.

5. The method of claim 4 wherein said dye and said carbonyliimidazole are combined in the presence of N,N-dimethyl formamide.

6. The method of claim 4 wherein said mixture is reacted for 2 hours.

7. The method of claim 4 wherein N-hydroxyphthalimide is added to said mixture at a concentration of about 2 equivalents.

8. The method of claim 4 comprising the additional step of stirring said final mixture for between about 5 and 12 hours.

9. The method of claim 8 comprising the additional step of combining said final mixture with ethyl acetate.

10. The method of claim 9 comprising the additional step of separating a resulting precipitate which comprises the desired activated dye.

11. The method of claim 10 wherein said separating step is performed by filtration and involves the additional step of drying said isolated precipitate.

12. The method of claim 4 wherein said dye is Cy5.

13. The method of claim 12 wherein the first combining step occurs in the presence of DMF, and said dye and said carbonyliimidazole are stirred at ambient for approximately 2 hours.

14. The method of claim 13 wherein said dye is present in said combining step at about 0.256 mmol, and said carbonyliimidazole is present in said combining step at about 0.64 mmol.

15. The method of claim 14 comprising the addition step, subsequent to said adding step, of stirring said final mixture for between about 5 and about 12 hours.

16. The method of claim 15 comprising the additional step of pouring said final mixture into a solution comprising about 150 ml of ethyl acetate.

17. The method of claim 16 comprising the additional step of isolating a resulting solid from said final mixture by vacuum filtration.

18. The method of claim 17 comprising the additional step of washing said resulting solid after vacuum filtration with ethyl acetate.

19. The method of claim 18 comprising the additional step of drying said resulting solid after washing by storing in a vacuum dessicator.

20. A method for preparing a dye-labeled chain terminator of claim 3 comprising:

combining a suitable activated dye with a dideoxynucleotide phosphate to form a mixture.

21. The method of claim 20 wherein said combining step occurs in the presence of an $HCO_3^-/CO_3^{2-}$ buffer.

22. The method of claim 21 wherein said combining step occurs at room temperature for between about 1 and about 16 hours.

23. The method of claim 20 comprising the additional step of isolating said chain terminator from said mixture by preparative thin-layer chromatography on silica gel using a $CH_2Cl_2/CH_3OH$ mixture in an approximately 1:1 ratio.

24. The method of claim 23 comprising the additional step of further purifying said chain terminator by reverse phase high performance liquid chromatography.

25. The dye-labeled chain terminator of claim 3, wherein X is an aminopropynyl group.

* * * * *